(12) United States Patent
Ostrander et al.

(10) Patent No.: US 6,433,154 B1
(45) Date of Patent: Aug. 13, 2002

(54) FUNCTIONAL RECEPTOR/KINASE CHIMERA IN YEAST CELLS

(75) Inventors: Darin B. Ostrander, Princeton, NJ (US); Jessica A. Gorman, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/085,720

(22) Filed: May 27, 1998

Related U.S. Application Data

(60) Provisional application No. 60/049,444, filed on Jun. 12, 1997.

(51) Int. Cl.[7] .................. C07N 21/04; C12N 15/00; C12N 15/63; C07K 14/00
(52) U.S. Cl. ................. 536/23.4; 536/24.31; 536/23.1; 435/69.1; 435/320.1; 435/325; 435/252.3; 435/17.3; 435/235; 435/255.2; 530/350; 530/351
(58) Field of Search .................. 536/24.31, 23.4, 536/23.1; 435/69.1, 320.1, 325, 253.3, 172.3, 235.1, 255.2; 530/350, 300

(56) References Cited

U.S. PATENT DOCUMENTS

| | | | |
|---|---|---|---|
| 5,218,090 A | | 6/1993 | Connors ..................... 530/350 |
| 5,717,067 A | * | 2/1998 | DiFiore et al. ............. 530/350 |
| 5,914,237 A | * | 6/1999 | Godowski et al. .......... 435/7.21 |
| 5,925,548 A | * | 7/1999 | Bruce et al. ................ 530/350 |
| 5,939,306 A | * | 8/1999 | Alex et al. ................ 435/253.3 |
| 5,945,523 A | | 8/1999 | Ullrich et al. ............. 536/23.5 |

OTHER PUBLICATIONS

Rudinger, J et al., Peptide Hormones, ed. J. A. Parsons, University Park Press, Baltimore, pp. 1–7, 1987.*
Yarden, et al. "Growth Factor Receptor Tyrosine Kinases" Ann. Rev. Biochem. 1988 57:443–78.
Aaronson "Growth Factors and Cancer" Science, Nov. 22, 1991, vol. 254: 1146–1153.
Posada, et al. "Molecular Signal Integration. Interplay Between Serine, Threonine, and Tyrosine Phosphorylation" Molecular Biology of the Cell, Jun. 1992, vol. 3, 583–592.
Kishimoto, et al. "Interleukin–6 and Its Receptor: A Paradigm for Cytokines" Science, Oct. 23, 1992, vol. 258: 593–597.
Mager, et al. "Osmostress Response of the Yeast *Saccharomyces*" Molecular Microbiology (1993) 10(2), 253–258.
Brewster, et al. "An Osmosensing Signal Transduction Pathway in Yeast"Science, Mar. 19, 1993, vol. 259: 1760–1763.
Chiba, et al. "Tyrosine Kinase Activation Through the Extracellular Domains of Cytokine Receptors"Nature, Apr. 15, 1993, vol.362: 646–648.
Ota, et al. "A Yeast Protein Similar to Bacterial Two–Component Regulators" Science, Oct. 1993, vol. 262: 566–569.
Maeda, et al. "A Two–Component System That Regulates An Osmosensing MAP Kinase Cascade in Yeast" Nature, May 19, 1994, vol.369: 242–245.
Maeda, et al. "Activation of Yeast PBS2 MAPKK by MAPKKKs or Binding of an SH3–Containing Osmosensor" Science, Jul. 28, 1995, vol.269: 554–558.
Posas, et al. "Yeast HOG1 MAP Kinase Cascade Is Regulated by a Multistep Phosphorelay Mechanism in the SLN1–YPD1–SSK1 "Two–Component" Osmosensor", Cell, Sep. 20, 1996, vol. 86:865–875.
Varela, et al. "Response of *Saccharomyces cerevisiae* to Changes in External Osmolarity" Microbiology (1996) 142: 721–731.
Ketela, et al. "Yeast Skn7p Activity is Modulated by the Sln1p–Ypd1p Osmosensor and Contributes to Regulation of the HOG Pathway" Mol. Gen. Genet (1998) 259:372–378.

* cited by examiner

*Primary Examiner*—Yvonne Eyler
*Assistant Examiner*—Nirmal S. Basi
(74) *Attorney, Agent, or Firm*—Rosemarie R. Wilk-Orescan

(57) ABSTRACT

A functional mammalian growth factor receptor/yeast histidine kinase chimera in Saccharomyces cerevisiae. In a preferred embodiment, the extracellular domain of the human epidermal growth factor receptor has been fused to the intracellular kinase domain of the SLN1 gene. The SLN1 gene encodes the plasma membrane sensor kinase of the yeast high osmolarity/glycerol response MAP kinase pathway. The chimeric protein is almost completely nonfunctional because the EGFR ECD is not capable of dimerization in the absence of ligand. In the presence of ligand, however, the chimeric kinase is activated and phosphorylation through the pathway is quantitatively repressed. This measure of pathway activity can be utilized to identify agonists and antagonists of the EGFR and other tyrosine kinase growth factor receptors in yeast cells.

3 Claims, 5 Drawing Sheets

Figure 3a
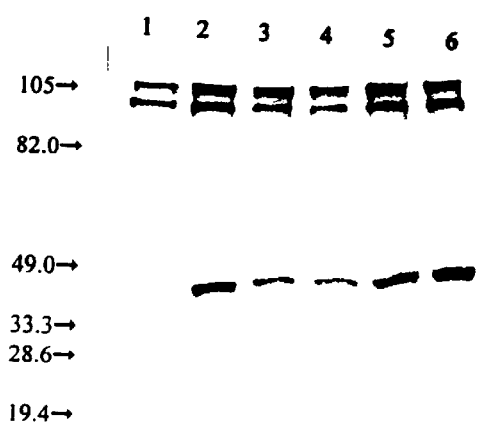
Figure 3b
Figure 3

FUNCTIONAL RECEPTOR/KINASE CHIMERA IN YEAST CELLS

CROSS-REFERENCE TO RELATED APPLICATION

This application claims the benefit of U.S. Provisional Application No. 60/049,444 filed Jun. 12, 1997.

FIELD OF THE INVENTION

The present invention concerns processes for detection of ligand binding, as well as yeast cells, nucleic acids, vectors and fusion proteins useful therefor.

BACKGROUND OF THE INVENTION

In order to identify novel agonists and antagonists of mammalian receptor tyrosine kinases (RTK), we wished to express the extracellular domains (ECD) of these single transmembrane proteins in a microorganism. The yeast *Saccharomyces cerevisiae* is an extremely well-studied unicellular eukaryote for which a vast array of genetic and biochemical methodologies are available. Although yeast does not possess tyrosine kinase receptors, it has been shown to utilize numerous mitogen-activated protein kinase (MAPK) pathways that are activated by plasma membrane protein receptors. We chose one of these pathways, the HOG (high-osmolarity/glycerol) pathway, in an attempt to model RTK-ligand binding functions.

Yeast respond to high external osmolar conditions by increasing the intracellular concentration of glycerol. Varela et al. (1996), *Microbiology* 142: 721–31. The HOG MAP kinase pathway in yeast (FIG. 1) consists of a histidine/aspartate/histidine/aspartate kinase relay coupled to a MAP kinase cascade. The SLN1 gene encodes the first histidine/aspartate kinases and functions as the plasma membrane sensor protein for the system. Under normal growth conditions, the Sln1 protein, a two-transmembrane (TM) plasma membrane kinase, is dimerized and actively transfers a phosphate to another protein, YPD1p, which in turn transfers the phosphate to another protein SSK1p. Posas et al. (1996), *Cell* 86: 865–75. Under high osmolar conditions, however, the Sln1 protein is deactivated. The lack of phosphorelay through the histidine/aspartate (HDHD) pathway causes phosphorylation and activation of the HOG MAPK pathway. Unphosphorylated Ssk1 actively phosphorylates the MAPKKK's, Ssk2 and Ssk22, which transfer the phosphate to the MAPKK, Pbs2, which in turn transfers the phosphate to the MAPK, Hog1. Phosphorylated Hog1 has been shown to activate transcription factors which increase production of enzymes involved in glycerol synthesis and stress response. Schuller et al. (1994), *EMBO I* 13: 4382–9.

SUMMARY OF THE INVENTION

By substituting the ECD of receptor tyrosine kinases (RTK) for that of such sensors as Sln1 protein, we model the ligand binding function of the ligand-binding proteins in yeast. This invention thus concerns *Saccharomyces cerevisiae* cells comprising a fusion protein having:

(a) an extracellular ligand-binding domain derived from a protein of interest, and (b) an intracellular kinase domain that is activated upon binding of a ligand;

wherein binding of a ligand is signaled by transfer of a phosphate by the intracellular domain. The invention also concerns the nucleic acid encoding the fusion protein, the associated vector, and the fusion protein itself.

The invention also concerns a process for detecting binding of a ligand to a protein of interest, which comprises:

(a) treating a culture of such cells with a test substance, and (b) detecting activation of the intracellular kinase domain. One manner in which the detecting step may be carried out is by the detection of phosphorylation of Hog1, a method for which is described in detail hereinafter.

In preferred embodiments, the intracellular kinase domain is derived from SLN1; the extracellular ligand binding domain from a mammalian receptor tyrosine kinase. In a preferred application of the invention, the extracellular ligand binding domain is derived from human epidermal growth factor receptor. The preferred *Saccharomyces* cells are strain SDO158 (BMS Culture Collection Accession Number SGY1661).

BRIEF DESCRIPTION OF THE DRAWINGS

FIG. 2A shows wild-type protein with inserted silent restriction sites (arrows); FIG. 2B, ΔTM1 construction deleted for amino terminal intracellular and first transmembrane domains; FIG. 2C, SKD construction (soluble kinase domain).

FIG. 3 shows HOG phosphorylation. Antiphosphotyrosine western analysis of immunoprecipitated Hog1. FIG. 3A corresponds to rich medium; FIG. 3B, defined medium. Odd numbered lanes correspond to low osmolar conditions; even numbered lanes, high osmolar conditions. Lanes 1 and 2 show wild type SLN1 gene with silent restriction sites (see FIG. 2A); lanes 3 and 4, ΔTM1 SLN1 construction (see FIG. 2B); lanes 5 and 6, SKD SLN1 construction (see FIG. 2C).

DETAILED DESCRIPTION OF THE INVENTION

Use and Utility

Figure 1:
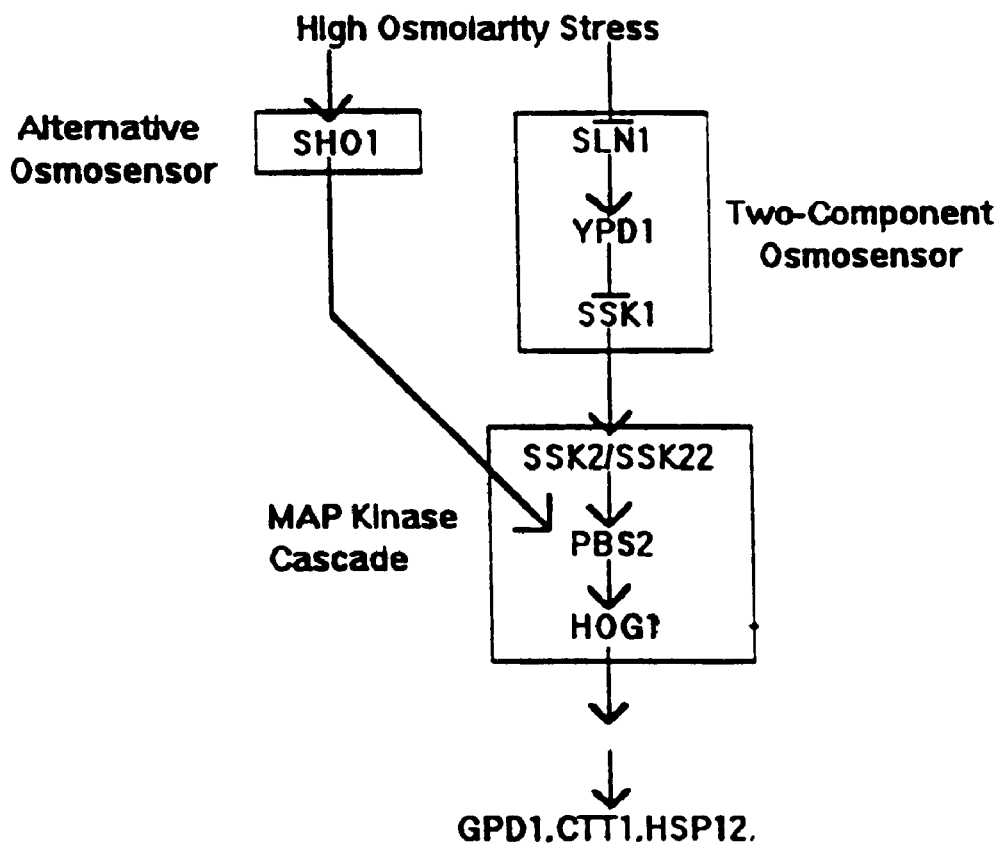
FIG. 1 shows the HOG pathway in yeast.

Persons of ordinary skill in the art will readily understand how to use the subject invention. The cells having the fusion construct may be used to screen for compounds and/or natural products that bind to the extracellular domain. Such ligands would be useful as agonists or antagonists (e.g., competitive inhibitors) of the protein from which the extracellular domain was derived. One can assay for different compound activities by selecting different extracellular domains. Additional methods of using the nucleic acids, polypeptides, expression vectors and host cells are apparent from the present specification.

Process of Preparation

Gene Constructs

The nucleic acids used in the present invention may be prepared by recombinant nucleic acid methods. See, for example, the recombinant DNA methods of Sambrook et al. (1989), Molecular Cloning: A Laboratory Manual, Second Edition, Cold Spring Harbor Laboratory, Cold Spring Harbor, N.Y.

The DNA sequences may be derived from a variety of sources, including genomic DNA, subgenomic DNA, cDNA, synthetic DNA, and combinations thereof. Genomic and cDNA may be obtained in a number of ways. Cells coding for the desired sequence may be isolated, the genomic DNA fragmented (e.g., by treatment with one or more restriction endonucleases), and the resulting fragments cloned, identified with a probe complementary to the desired sequence, and screened for the presence of a sequence coding for the desired activity.

For cDNA, the cDNA may be cloned and the resulting clone screened with a probe for cDNA coding for the desired region. The desired DNA sequence may also be isolated by expression screening. Upon isolation of the desired clone, the cDNA may be manipulated in substantially the same manner as the genomic DNA.

Another method of deriving DNA sequences is through the use of the polymerase chain reaction with a pair of suitable homologous oligodeoxynucleotides. See, for example, Saiki et al. (1988), *Science* 239: 487.

To form the chimeric gene constructs, DNA fragments may be ligated in accordance with conventional techniques known in the art. Such techniques include use of restriction enzymes to convert sticky-ended fragments to blunt ends (or vice-versa), polymerases and nucleotides to fill in sticky ends to form blunt ends, alkaline phosphatase to avoid undesired ligations, and ligases to join fragments. An additional method used to modify DNA sequences to facilitate subcloning is the creation of restriction sites by site-directed mutagenesis.

Expression Vectors

Expression vehicles for production of the molecules of the invention include plasmids or other vectors. In general, such vectors contain control sequences that allow expression in various types of hosts. Suitable expression vectors containing the desired coding and control sequences may be constructed using standard recombinant DNA techniques known in the art, many of which are described in Sambrook et al. (1989), *Molecular Cloning: A Laboratory Manual*, Second Edition, Cold Spring Harbor Laboratory, Cold Spring Harbor, N.Y.

An expression vector as contemplated by the present invention is at least capable of directing the replication of the vector in both bacteria and yeast and expression of the DNA sequence of interest. In the present example, this includes a transmembrane domain coupled between an intracellular domain and an extracellular domain. One class of vectors utilizes yeast DNA elements that provide autonomously replicating origins such as the yeast $2\mu$ element or ARS1 sequence which yield extrachromosomal plasmids. A second class of vectors relies upon the integration of the desired gene sequences into the host cell chromosome. The vectors must also incorporate a bacterial origin of replication. Suitable bacterial origins of replication include, for example, the ColE1, pSC101 and M13 origins of replication.

Expression vectors useful in the present invention typically contain a promoter located 5' to (i.e., upstream of) the DNA sequence to be expressed, and a transcription termination sequence located 3' to (i.e., downstream of) the sequence to be expressed. Suitable promoters include, for example, the yeast ADH1 promoter. The promoter sequence may also be inducible, to allow modulation of expression (e.g., by the presence or absence of nutrients or other inducers in the growth medium). Examples include the yeast GAL1, CUP1 and MET25 promoters. Suitable termination sequences include, for example, the yeast CYC1 termination and polyadenylation sequences.

The expression vectors may also include other regulatory sequences for optimal expression of the desired product. Such sequences include secretory leader sequences, which provide for secretion of the expression product or direct membrane localization, and restriction enzyme recognition sequences, which provide sites for cleavage by restriction endonucleases. All of these materials are known in the art and some are commercially available.

A suitable expression vector may also include marking sequences, which allow phenotypic detection and/or selection of transformed yeast or bacterial cells. Such a marker may provide prototrophy to an auxotrophic host (e.g., amino acid biosynthetic genes), biocide resistance or supersensitivity (e.g., antibiotic resistance) or a phenotypically detectable signal (e.g., fluorescence). The selectable marker gene can either be directly linked to the DNA gene sequences to be expressed, or introduced into the same cell by co-transfection. Examples of yeast selectable markers include the *Basidium pullulans* AUR1-C gene, the yeast URA3 or LEU2 genes and the like. Examples of bacterial selectable markers include the ampicillin resistance gene. A preferred vector is pDO105, containing the ColE1 and $2\mu$ origins of replication, the yeast LEU2 and bacterial $amp^R$ genes, and the yeast ADH1 promoter sequence (BMS Culture Collection Accession Number SGB1580).

In a further alternative, the constructs may be introduced into a cell by transformation in conjunction with a gene allowing for selection where the construct will become integrated into the host genome or persist episomally. Usually, the construct will be part of a vector having homologous sequences for integration or a replication system recognized by the host cell.

Host Cells

The present invention additionally concerns hosts for the chimeric gene constructs. Suitable host cells include *Saccharomyces cerevisiae* cells in which endogenous activities do not interfere with the function of the chimeric protein under study. Such *S. cerevisiae* strains include strain SDO158 (BMS Culture Collection Accession Number SGY1661) and the like.

Expression vectors may be introduced into host cells by various methods known in the art. For example, transformation of host cells with expression vectors can be carried out by the alkali cation method. However, other methods for introducing expression vectors into host cells, for example, electroporation and spheroplast transformation can also be employed. Host cells containing an expression vector may be identified by any of a number of methods known in the art.

DETAILED DESCRIPTION OF PREFERRED EMBODIMENTS

Methods

Strains

Yeast manipulations employed standard methodologies; see, for example, Kaiser et al. (1994), *Methods in Yeast Genetics: A Laboratory Course Manual*. Yeast transformations were performed by electroporation using a Gene Pulsar (Bio-Rad). Becker et al. (1991), *Methods Enzymol* 194:

182–7; Ostrander et al. (1994), *Gene* 148: 179–85. Dr. I. Ota provided the SLN1/sln1 heterozygous strain (his3-Δ200/his3-Δ200, leu2-3,112/leu2-3,112,lys2-801/lys2-801, SLN1/sln1Δ::HIS3,trp1-1/trp1-1, ura3-52/ura3-52. Ota et al. (1993), *Science* 262: 566–9). Expression of various SLN1 constructs was tested in strain W303-1A (ade2-1,can1-100, his3-11,15,leu2-3,112, trp1-1,ura3-1,MATa, gift of R. Rothstein). The NIH/3T3 cell line stably expressing EGFR (HER1) was created and provided by Dr. B. Cohen.

Strains containing a disruption of the sho1 allele were created by integrative transformation of the 4.5 kb PCR product resulting from amplification of plasmid NKY51 (Alani et al., (1987), *Genetics* 116: 521) with oligonucleotides containing both SHO1 and pNKY51 sequences ATTAATATAAACAATCCAAGTCAAGT-CAATGACAGTCATAAG TGCGGCGACGATAGT-CAT (SEQ. ID. NO.: 1) and TATCAGCTTTCTTTGCTCAACA-GAATCGCTACACGGAAATGTT GAATACTCAT-ACTCTTC (SEQ. ID. NO.: 2). All sequences are shown in 5'-to-3' orientation unless otherwise noted.

The PCR reaction amplifies the URA3 gene with flanking direct repeats of fragments of the *S. typhimurium* HisG gene. The oligonucleotides contain 30 bp each homologous with regions flanking the SHO1 open reading frame. When the construct is integrated at the SHO1 locus, cells in which homologous recombination between the HisG repeats have caused loss of the URA3 gene can be selected by growth on 5-FOA media.

Reagents

Site directed mutagenesis was performed using the QuikChange Mutagenesis System (Stratagene). Oligonucleotides were obtained from GenoSys. Protein gels of various SLN1 constructions were 7.5–15% gradient acrylamide using the Vertical Slab Gel Unit (Hofer). Mouse anti-human epidermal growth factor receptor extracellular domain monoclonal antibody and recombinant EGF ligand were obtained from Upstate Biotechnology.

Plasmids

Plasmid and *Escherichia coli* manipulations employed standard methodologies. Sambrook et al, (1989), *Molecular Cloning: A Laboratory Manual*, 2nd ed. Cold Spring Harbor Laboratory Press, Cold Spring Harbor. The SLN1 expression vector was created as follows: A 1.15 kb DNA fragment containing the ADH1 promoter was isolated from vector pDB20 (Becker et al, (1991), *Proc Natl Acad Sci USA* 88: 1968) with BamHI and PstI. This fragment was inserted into the high-copy, LEU2 plasmid YEpLac181 using the same restriction sites. Gietz et al. (1988), *Gene* 74: 527–34. This vector was cut with NotI and PstI and the annealed oligonucleotides GGCCGCATATGCTAGCTAAGCTCTAGAC-CAAGAACGCGTCTGCA (SEQ. ID. NO.: 3) and GACGCGTTCTTGGTCTAGAGCT-TAGCTAGCATATGC (SEQ. ID. NO.: 4) were inserted in order to create a multiple cloning sequence behind the ADH1 promoter.

The carboxyl terminal region of the SLN1 gene was isolated from vector pSLN1 (provided by I. Ota) with MluI and XbaI. Ota et al (1993), *Science* 262: 566–9. This fragment was inserted into the modified ADH1 promoter vector using the same restriction sites. The amino terminal domain of the SLN1 gene was cloned from total genomic DNA of strain Y294 (Fedor-Chaiken et al. (1990), *Cell* 61: 329–40) by PCR using oligonucleotides ATAGAATTCATATGCGATTTGGCCTGCCATCAAA (SEQ. ID. NO.: 5) and GGTTTTTGCTTCATTTGCGGCCTCTGCCTCAATC (SEQ. ID. NO.: 6). This PCR product was blunt-end ligated into plasmid BlueScript II (SK-) (Stratagene) cut with EcoRV. Site-directed mutagenesis was effected by two oligonucleotides and their complements:

ATTTTACCTCGAgCTATAAAAATTT (SEQ. ID. NO.: 7) added a XhoI site just after the first transmembrane domain, and TCCAGCAACGAAgCTAGCAAAAATC (SEQ. ID. NO.: 8) added a NheI site just before the second transmembrane domain. The second mutation is silent while the first created a conservative amino acid substitution (N49S). The mutagenized amino terminal region of the SLN1 gene was isolated as an NdeI-XbaI and added to the vector containing the carboxyl terminal region of Sln1 using the same restriction sites.

In order to create the SLN1ΔTM1 construct, which is deleted for the amino terminal and first transmembrane domains, the SLN1 expression vector was cut with NdeI and XhoI, deleting the amino terminal intracellular and TM1 domains, and the annealed oligonucleotides TAGATATCATGTCATACAAG (SEQ. ID. NO.: 9) and TCGACTTGTATGACATGATATC (SEQ. ID. NO.: 10) were inserted. The new 5' sequence encodes the STE3 signal sequence, MSYKS (Hagen et al. (1986), *Proc Natl Acad Sci USA* 83: 1418–22) to direct the protein to the plasma membrane. The resulting protein has a predicted molecular mass of 130 kDa compared with wild-type Sln1, which is 134 kDa. The SKD (soluble kinase domain) expression plasmid was created by cutting the SLN1 expression vector with NotI and NcoI, blunt ending with Klenow fragment and religating. The resulting protein has a predicted molecular mass of 87.4 kDa.

In order to add a CAAX box to the carboxyl terminus of the SLN1 kinase domain, a silent restriction site was inserted at the end of the gene using site-directed mutagenesis. The carboxyl terminus was isolated on a small plasmid by cutting the SLN1 expression vector with EcoRV and NruI and religating. The vector was then mutagenized with the oligonucleotide GAAAAATAACAAATGtACAACCAAGAATAGT (SEQ. ID. NO.: 11), adding a silent BsrGI site near the end of the open reading frame. This vector was then cut with BsrGI and MluI and the annealed oligonucleotides GTACATGTATTATAAGTTAATAAGAATTCA (SEQ. ID. NO.: 12) and CGCGTGAATTCTTATTAACTTATAATACAT (SEQ. ID. NO.: 13) were inserted. This sequence adds the amino acids CIIS of the RAS2 gene (Powers et al. (1984), *Cell* 36: 607–12) to the carboxyl terminus of the SLN1 gene. This modified carboxyl terminus was subsequently isolated with NcoI (which was blunt ended with Klenow fragment) and MluI and inserted into the ADH1 promoter vector described above cut with NotI (blunt-ended with Klenow) and MluI. This construction effectively recreates the kinase domain expression vector described previously.

In order to replace the extracellular domain of SLN1 with a leucine zipper sequence, the relevant sequence from a C/EBP clone (Landschulz et al. (1988), *Genes Dev.* 2: 786–800) was isolated by PCR with oligonucleotides GGCCGCTCGAGCAAAGCCAAACAGCG-CAACGTGG (SEQ. ID. NO.: 14) and GGCTAGCTAGCTTCAAGGAGCTCTCAG-GCAGCTGG (SEQ. ID. NO.: 15). This fragment was cut with NheI and XhoI and inserted into the SLN1 expression vector using the same restriction sites. In order to make the construction single-transmembrane, this vector was cut with NdeI and XhoI and the same STE3 signal sequence oligonucleotides added as described above. Site-directed mutagenesis (QuikChange Kit, Stratagene) was employed to alter the central leucine (35) to a proline with the oligonucleotide GCGGGTGGAA CAGCcGAGCC GTGAACTGG (SEQ. ID. NO.: 16) and its complement. This mutation also removes a PvuII site from the sequence. The mutation was verified by DNA sequencing.

The ECD of EGFR was subcloned by PCR of a vector containing the EGFR cDNA in pCDM8 (Invitrogen) with oligonucleotides TATCTCGAGTGGGACGGCCGGGGCAGCGCT (SEQ. ID. NO.: 17) and TAGTGCTAGCTTAGGCCCATTCGTTGGAC (SEQ. ID. NO.: 18). This product was cut with NheI and XhoI and inserted into the SLN1 expression vector with the same restriction sites. The resulting protein's predicted molecular mass is 174 kDa. The protein was made single-transmembrane by cutting with NdeI and XhoI and adding the STE3 oligonucleotides described previously. The predicted size of this protein is 169 kDa.

Antisera

To create antisera to the carboxyl terminal region of Sln1, a DNA fragment encoding amino acids 494-1220 was excised from the SLN1 expression vector with AflIII (blunt-ended with Klenow Fragment) and BglII. The fragment was ligated into the vector pMAL-C2 (New England Biolabs) cut with HindIII (blunt-ended with Klenow) and BamHI in order to create a MalE/Sln1 fusion protein. IPTG induction of this plasmid in *E. coli* produced large amounts of a 124 kDa fusion protein. A cell extract was prepared and the fusion protein was bound to an amylose column and eluted with maltose. The Sln1 fusion protein was purified by preparative electrophoresis, electroeluted, dialyzed and concentrated. The protein was injected into rabbits and antisera isolated as previously described. Ostrander et al. (1995), *I Biol Chem* 46: 27045–50.

The HOG1 open reading frame was cloned from total genomic Y294 (Fedor-Chaiken et al. (1990), *Cell* 61: 329–40) DNA by PCR using oligonucleotides CCGGCCGGCGCGCCCTCGAGCGGC-CGCGCTTTGCAGCTACATGA TCGCTGAC-CTTTGTTTCCACCAGC (SEQ. ID. NO.: 19) and GGCCGGCATATGACCACTAACGAGGAAT-TCATTAGGACACAG ATATTCGG (SEQ. ID. NO.: 20). The product was cut with NdeI and XhoI and ligated into pET23B (Novagen) with the same restriction sites in order to create a HIS$_6$-tagged HOG1 construct. IPTG induction of this plasmid in *E. coli* produced a 45 kDa product. The protein was isolated on a Ni-NTA agarose column (Qiagen) and utilized to create antisera as described above.

Hog1 Phosphorylation Assay

Strains were grown in YPD (1% yeast extract, 2% peptone, 2% glucose) with (high osmolarity conditions) or without (low osmolarity conditions) 1 M sorbitol or 0.3 M NaCl at 28 °C. Subsequent steps were performed at 5° C. Log phase cultures ($2-3\times10^7$ cells/ml) were harvested by centrifugation. Cells were broken in protein isolation buffer (25 mM HEPES (pH 7.4), 10% glycerol, 1 mM Na$_2$EDTA) with protease inhibitors (87 µg/ml PMSF, 2.5 µg/ml TLCK, 0.75 µg/ml pepstatin A, 0.5 µg/ml leupeptin, 0.5 µg/ml aprotinin) with 500 micron-diameter acid-washed glass beads (Sigma) in a Mini-Bead Beater (BioSpec Products). Total protein concentration was determined with the Bicinchoninic Acid Protein Assay (Sigma). Aliquots containing 100 µg total protein were used for immunoprecipitation (Sambrook et al. (1989), *Molecular Cloning: A Laboratory Manual*, 2nd ed. Cold Spring Harbor Laboratory Press) with 10 µl anti-Hog1 antisera and 5 mg protein A Sepharose CL-4B (Pharmacia). In order to remove the IgG from the final immunoprecipitate, the final washed pellets were resuspended in 1% SDS and centrifuged (Harlow et al. (1988), *Antibodies: A Laboratory Manual*. Cold Spring Harbor Laboratory Press). Supernatants were collected and placed in SDS-PAGE loading buffer.

Western analysis utilized 10% Ready Gels in the Mini-Protean Cell System (Bio-Rad) which were blotted to PVDF membranes in a Mini-V8 Apparatus (Life Technologies). Western analyses used the PhotoBlot Chemiluminescent Detection System (Gibco-BRL). Rabbit polyclonal anti-phosphotyrosine antisera was obtained from Transduction Laboratories. Western autoradiograms were quantitated on an Ultroscan Enhanced Laser Densitometer (LKB Bromma).

Cell Fractionation and Membrane Localization

Cells were grown and harvested as described above. Cells were broken with glass beads in membrane isolation buffer (300 mM sucrose, 50 mM Tris-HCl (pH 7.5), 10 mM b-mercapto ethanol, 1 mM Na$_2$EDTA) and protease inhibitors at 5° C. Unbroken cells and glass beads were removed by centrifugation at 1000×g for 5 minutes. Membrane and cytosolic fractions were separated by centrifugation at 100,000×g for 1 hour at 5° C. in a TL-100 ultracentrifuge (Beckman). Pellets (membrane fractions) were directly resuspended in SDS-PAGE loading buffer, while supernatants (cytosol) were first concentrated with a Centricon-10 Concentrator (Amicon) centrifuged at 4500×g for four hours at 5° C. Plasma membranes were isolated and tested as previously described. Ostrander et al. (1995), *I. Biol. Chem.* 46: 27045–50.

Radio-Ligand Binding Studies

Membrane extracts were isolated as described, but were resuspended in 100 µl membrane storage buffer (20% glycerol, 50 mM Tris-HCl (pH 7.5), 1 mM DTT). 1 ng recombinant human 3-[$^{125}$I]iodotyrosyl-EGF at 3.7 Mbq/ml (0.2 µCi) (Amersham) was added to 25 µl membrane extract in membrane storage buffer with 1% BSA. 100 ng unlabeled EGF was added to competition controls. After incubation for 1 hour at 30° C., membranes were reisolated by centrifugation at 100,000×g. The supernatants were discarded and the pellets washed once with membrane storage buffer. The pellets were counted in a Cobra Auto-Gamma Counter (Packard).

Results

Sln1 Kinase Domain Complementation

Figure 2:
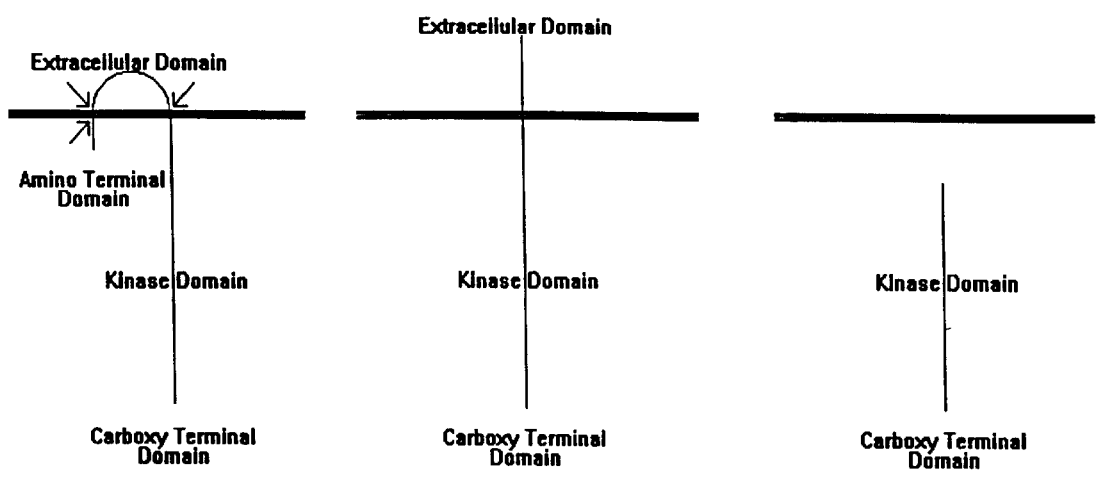
FIG. 2 shows various truncation constructions of SLN1.

Sln1 protein is different than that of RTK receptors in that Sln1 possesses two TM domains. In order to test constructs in which the amino terminus of the receptor was untethered and extracellular, an SLN1 clone into which contained three restriction sites were inserted by site-directed mutagenesis was created (FIG. 2A). The amino terminal intracellular and first TM domains of Sln1 were deleted and substituted with a protein export signal sequence (ΔTM1) (FIG. 2B). As an additional control, a vector for the expression of only the soluble kinase domain (SKD) was constructed (FIG. 2C). Synthesis of the protein encoded by each construction was tested by western analysis with polyclonal antisera against the intracellular region of Sln1. The kinase domain was shown to be cytosolic by cell fractionation experiments while those containing TM domains were membrane-associated.

Deletion of the SLN1 gene is a lethal event in yeast cells presumably because high osmolarity and stress responses are constitutively activated. Ota and Varshavsky, (1993), *Science* 262: 566–569. Expressing chimeric proteins in an sln1Δ strain would therefore test the ability of the chimera to substitute for wild type SLN1. We transformed the SLN1 truncation expression plasmids into a diploid SLN1 heterozygote (SLN1/sln1Δ). The strains were then sporulated and the haploid progeny which contained any of the SLN1 expression plasmids were observed to be viable. If however the strain contained no plasmid or the parent plasmid without the SLN1 gene, only half of the progeny survived. These results demonstrate that each of our SLN1 truncation constructions were functional.

Hog1 Phosphorylation Assay

In order to observe the effect of the SLN1 truncations on signaling through the HOG kinase pathway, the extent of tyrosine phosphorylation of the Hog1 protein. Following isolation of total protein from yeast cells grown under different osmolar conditions, Hog1 was immunoprecipitated and western analyses performed with antiphosphotyrosine antisera.

When sln1Δ is complemented with the full-length SLN1 gene, Hog1 phosphorylation is observed to increase when cells are grown in high osmolar media (FIG. 3, lanes 1 and 2, respectively). Therefore, as in wild type cells, Sln1 is active in low osmolarity media and the HOG pathway is repressed. This situation is reversed in high osmolarity media; Sln1 is inactivated, and Hog1 phosphorylation is increased. In cells expressing sln1ΔTM1, the level of Hog1 phosphorylation is low and fails to show any change in response to an increase in the osmolarity of the media (FIG. 3, lanes 3 and 4). Therefore, without TM1, Sln1 appears to be constitutively active, and the HOG pathway is insensitive to changes in the osmolarity of the medium. When the SLN1 kinase domain alone is expressed, again no response to changes in osmolarity is observed. However, Hog1 appears to be fully phosphorylated (FIG. 3, lanes 5 and 6). Therefore, in the absence of the extracellular and TM domains, Sln1 histidine kinase seems to be inactive. In this case, the HOG pathway appears to be fully active as in high osmolarity media.

In order to confirm the hypothesis that the phosphorylation state of the HOG1 protein mirrors the phosphorylation state of the SLN1 protein, a DNA sequence encoding the FLAG epitope was added to the C-terminal end of the coding regions of the three truncation constructions. In all three cases, the constructions were able to complement sin1Δ lethality. Anti-FLAG monoclonal antibodies were shown to specifically immunoprecipitate proteins from these strains of the correct molecular weight, and these proteins were recognized by anti-Sln1 antisera on western blots. These strains were labeled with high activity orthophosphoric acid in phosphate-depleted media in low and high osmolarity media. Cells were harvested, broken, and membrane preparations isolated. (In the case of the kinase domain, the cytosol was isolated.) Anti-FLAG antibodies were used to immunoprecipitate Sln1 from these preparations, and the proteins were subjected to SDS-PAGE and blotted to membranes. Autoradiograms of these blots showed labeled bands at the predicted molecular weight for full-length and ΔTM1 Sln1. The latter result is consistent with our observation that in the ΔTM1 strain, Hog1 is constitutively dephosphorylated. The full-length labeled band was much darker for cells grown in low osmolar media than in high, consistent with the hypothesis that Sln1 is deactivated under high osmolar conditions. Western analysis of a duplicate blot demonstrated approximately equal amounts of Sln1 immunoprecipitated in each case. No labeling was observed for the SKD strain, even though a band of the correct molecular weight was present on the western blot. This is consistent with our observation that Hog1 is constitutively phosphorylated in this strain. These experiments provide evidence that the phosphorylation state of Hog1 mirrors that of Sln1. Therefore, Hog1 phosphorylation may be utilized as an in vivo measure of the activity of the various Sln1 constructions created in this study.

Sln1 Membrane Association and Dimerization

In order to test whether membrane association of SLN1 is essential for its regulation, a peptide sequence was added to the 3' end of kinase domain in order to direct it to the plasma membrane. A carboxyl terminal CAAX box has been shown to be farnesylated on the cysteine, and these proteins are found to be associated with the plasma membrane in yeast cells (Stokoe et al. (1994), *Science* 264:1463). Expression of the protein was observed by western analysis in wild type cells. This protein construction was observed to be associated with the plasma membrane by western analysis of subcellular fractions. Hog1 phosphorylation showed no differential related to changes in osmolarity, but was maximally phosphorylated in all cases as was observed with the derivative containing only the soluble kinase domain. This result suggests that membrane association alone is not sufficient to restore kinase activity.

In order to test the importance of Sln1 dimerization on its activity, we substituted a leucine zipper region from C/EBP for the ECD of the SLN1ΔTM1 construct. The Hog1 protein in these cells was only weakly phosphorylated under all conditions tested. Therefore this chimeric Sln1 derivative appears to be constitutively activated. However when the same zipper motif containing a mutation which altered the central leucine to a proline was substituted, Hog1 was constitutively highly phosphorylated. This suggests that the Sln1 kinase is activated only when the protein possesses an extracellular domain capable of dimerization.

EGFR/SLN1 Chimeras

In order to test the effects of coupling the ECD of a mammalian tyrosine kinase receptor to a MAP kinase cascade sensor protein in yeast cells, a DNA sequence encoding a chimeric protein in which the extracellular portion would be comprised of the ECD of EGFR and the transmembrane and intracellular portions (ICD) would be that of the Sln1 protein was constructed. The silent restriction sites were used to substitute the sequence encoding the ECD of the epidermal growth factor receptor (EGFR) for the sequence encoding the ECD of Sln1. Two constructions were created; one with both TM domains intact (FIG. 2A) and another with the first removed so that the ECD would be untethered as in mammalian cells (FIG. 2B). Expression of the constructions in wild type strains was demonstrated using western analysis with antisera generated to the kinase domain of Sln1 as well as with antibodies to the ECD of EGFR. The construction was found to be able to complement sln1Δ; the heterozygous strain demonstrated viability of all four spores in tetrad dissection experiments. The protein was also found to be associated with the plasma membrane in these strains.

If the EGFR ECD functions in yeast as it does in mammalian cells, it would be expected that the chimera would be unable to dimerize in the absence of ligand. The level of Hog1 phosphorylation was examined in the strains containing either the two TM or the single TM EGFR chimera. In both cases, Hog1 was maximally phosphorylated, unlike the strains expressing either full-length or ΔTM1 SLN1. This result suggested that the receptor chimeras do not dimerize in the absence of ligand. Therefore there is little activation of Sln1. However, no significant decrease in Hog1 phosphorylation was observed even in the presence of ligand up to a concentration of 0.1 mg/ml.

Ligand Binding

Figure 4:
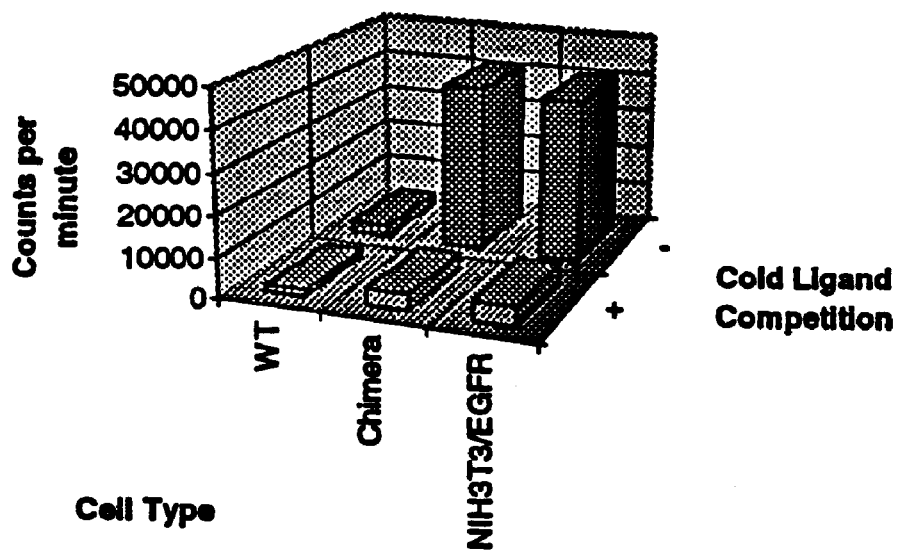
FIG. 4 shows radioligand binding to EGFR/SLN1 chimera. Wild type yeast cells, cells expressing the chimera construction, or NIH3T3 cells overexpressing EGFR were harvested and membrane preparations prepared. Radioligand with and without excess amounts of cold ligand were allowed to bind. The membranes were washed and quantitated in a scintillation counter.

To observe ligand interaction with the chimeric receptor, binding of $^{125}$I-tyrosyl-EGF to membrane extracts of cells expressing the EGFR/SLN1 chimeras was measured. Radioligand was observed to bind to membrane preparations which contained the chimeric receptor. The binding could be competed with cold ligand (FIG. 4). No binding was observed for membrane extracts from cells not expressing the chimera. As a control, NIH3T3 cells expressing EGFR were examined and shown to bind the radioligand, but not in the presence of excess cold ligand. These results demonstrate that the receptor chimeras made in these strains are capable of binding ligand.

SHO1 Deletion

Sho1 has been found to be a positive regulator of the HOG pathway (Maeda et al., (1995), *Science* 269: 554). Under high osmolarity conditions, the protein phosphorylates PBS2, the MAPKK of the HOG pathway (FIG. 1). It appeared that Sho1 might contribute to low-level phosphorylation of Hog1, even under low osmolarity conditions. Therefore its disruption might afford an observable reduction in Hog1 phosphorylation upon receptor dimerization. Therefore the SHO1 gene was disrupted in the chimeric and control strains.

Figure 5:
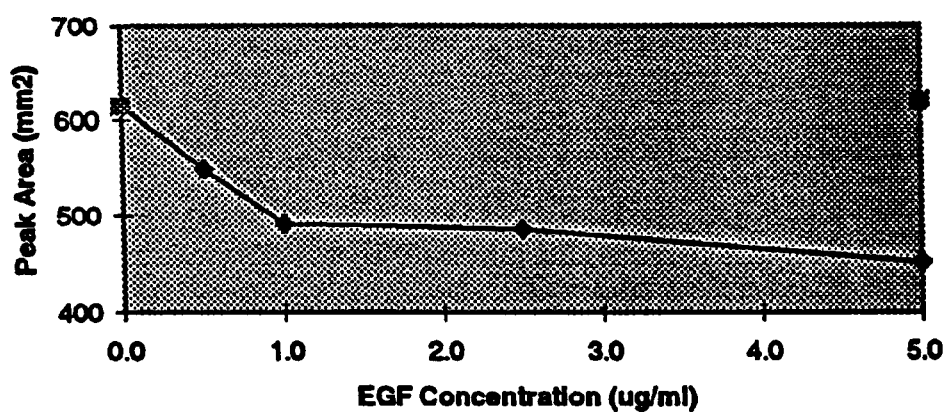
FIG. 5 shows HOG pathway signaling through the EGFR/SLN1 chimera in response to exogenous ligand. Strains expressing the chimera or the ΔTM1 SLN1 construction were grown in the presence of different concentrations of the ligand EGF. Cells were harvested, Hog1 was immunoprecipitated and the relative levels of phosphorylation were quantitated with antiphosphotyrosine.

We observed no difference in the levels of Hog1 phosphorylation between the SHO1 and sho1Δ strains containing the SLN1 truncation plasmids with the exception of wild-type SLN1. In the sho1Δ strain, Hog1 phosphorylation was slightly reduced in high osmolarity media. Likewise, no reduction in Hog1 phosphorylation with the 2-TM EGFR/SLN1 chimera strain in the presence of ligand was observed with the sho1 disruption. However a marked reduction in phosphorylation level was observed for the ΔTM1 EGFR/SLN1 chimera in the presence of ligand. We observed this decrease over a range of ligand concentrations (FIG. 5). These results suggest that EGF is binding to the chimeric receptor, causing its dimerization and functional activation and thus diminishing signaling through the HOG pathway.

Concluding Summary

An EGFR/SLN1 chimera has been successfully expressed in yeast cells. The chimeric gene is capable of functionally substituting for the SLN1 gene in an sln1Δ strain. Dimerization of the Sln1 kinase domain is necessary for the function of the kinase demonstrating that this system provides an excellent model for RTK ligand binding. The chimera binds ligand and is incapable of attenuating signaling through the HOG pathway in the absence of ligand. However, in a sho1Δ strain, the chimeric receptor reduces kinase signaling through the HOG pathway in the presence of ligand. It appears feasible to obtain similar results with other medically important RTKs and ligands. The corresponding strains can be utilized as screening vehicles in the discovery of novel therapeutics which effect ligand/RTK interactions.

Abbreviations

The abbreviations used throughout this specification have the following meanings, unless otherwise identified in specific instances.

| | |
|---|---|
| BSA | bovine serum albumin |
| DTT | dithiothreitol |
| ECD | extracellular domain |
| EDTA | ethylenediaminetetraacetic acid |
| EGF | epidermal growth factor |
| EGFR | epidermal growth factor receptor |
| FOA | fluoroorotic acid |
| HDHD | histidine/aspartate/histidine/aspartate |
| HOG | high-osmolarity/glycerol response |
| ICD | intracellular domain |
| IPTG | isopropyl β-D-thiogalactopyranoside |
| MAPK | mitogen-activated protein kinase |
| MAPKK | MAPK kinase |
| MAPKKK | MAPKK kinase |
| PAGE | polyacrylamide gel electrophoresis |
| PBS | polymyxin-B sensitivity |
| PMSF | phenylmethylsulfonyl fluoride |
| PVDF | polyvinylidene difluoride |
| RTK | receptor tyrosine kinase |
| SDS | sodium dodecyl sulfate |
| SKD | soluble kinase domain |
| SSK | suppresser of lethality of SLN1 kinase null |
| TLCK | Nα-p-tosyl-L-lysine chloromethyl ketone |

What is claimed is:

1. A *Saccharomyces cerevisiae* cell comprising a fusion protein, wherein the fusion protein comprises:
   a) an extracellular ligand-binding domain of human epidermal growth factor receptor;
   b) an intracellular kinase domain of SLN1 that is activated upon binding of a ligand to the extracellular ligand-binding domain of human epidermal growth factor receptor;
   wherein binding of the ligand is signaled by transfer of a phosphate by the intracellular domain to YPD1.

2. A nucleic acid encoding a fusion protein, wherein the fusion protein comprises:
   a) an extracellular ligand-binding domain of human epidermal growth factor receptor, and
   b) an intracellular kinase domain of SLN1 capable of transferring a phosphate to YPD1 upon binding of a ligand to the extracellular ligand-binding domain of human epidermal growth factor receptor.

3. A vector comprising the nucleic acid of claim 2.

* * * * *

SEQUENCE LISTING

```
<160> NUMBER OF SEQ ID NOS: 20

<210> SEQ ID NO 1
<211> LENGTH: 60
<212> TYPE: DNA
<213> ORGANISM: Artificial Sequence
<220> FEATURE:
<223> OTHER INFORMATION: Description of Artificial Sequence:
      Oligonucleotides containing both SHO1 and pNKY51
      sequences.
```

```
<400> SEQUENCE: 1
attaatataa acaatccaag tcaagtcaat gacagtcata agtgcggcga cgatagtcat      60

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence:
      Oligonucleotides containing both SHO1 and pNKY51
      sequences.

<400> SEQUENCE: 2
tatcagcttt ctttgctcaa cagaatcgct acacggaaat gttgaatact catactcttc      60

<210> SEQ ID NO 3
<211> LENGTH: 44
<212> TYPE: DNA
<213> ORGANISM: Artificial Sequence
<220> FEATURE:
<223> OTHER INFORMATION: Description of Artificial Sequence:
      Oligonucleotides inserted to create multiple
      cloning sequence.

<400> SEQUENCE: 3
ggccgcatat gctagctaag ctctagacca agaacgcgtc tgca                      44

<210> SEQ ID NO 4
<211> LENGTH: 36
<212> TYPE: DNA
<213> ORGANISM: Artificial Sequence
<220> FEATURE:
<223> OTHER INFORMATION: Description of Artificial Sequence:
      Oligonucleotides inserted to create multiple
      cloning sequence.

<400> SEQUENCE: 4
gacgcgttct tggtctagag cttagctagc atatgc                               36

<210> SEQ ID NO 5
<211> LENGTH: 34
<212> TYPE: DNA
<213> ORGANISM: Artificial Sequence
<220> FEATURE:
<223> OTHER INFORMATION: Description of Artificial Sequence:
      Oligonucleotides to clone amino terminal domain
      SLN1 gene.

<400> SEQUENCE: 5
atagaattca tatgcgattt ggcctgccat caaa                                 34

<210> SEQ ID NO 6
<211> LENGTH: 34
<212> TYPE: DNA
<213> ORGANISM: Artificial Sequence
<220> FEATURE:
<223> OTHER INFORMATION: Description of Artificial Sequence:
      Oligonucleotides to clone amino terminal domain
      SLN1 gene.

<400> SEQUENCE: 6
ggtttttgct tcatttgcgg cctctgcctc aatc                                 34

<210> SEQ ID NO 7
<211> LENGTH: 25
<212> TYPE: DNA
<213> ORGANISM: Artificial Sequence
```

```
<220> FEATURE:
<223> OTHER INFORMATION: Description of Artificial Sequence:
      Oligonucleotide to effect mutagenesis to add a
      XhoI site.

<400> SEQUENCE: 7
attttacctc gagctataaa aattt                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide to add NheI site before 2nd
      transmembrane domain.

<400> SEQUENCE: 8
tccagcaacg aagctagcaa aaatc                                    25

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:
      oligonucleotide with complement encodes the STE3
      signal sequence.

<400> SEQUENCE: 9
tagatatcat gtcatacaag                                          20

<210> SEQ ID NO 10
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide with complement encodes the STE3
      signal sequence.

<400> SEQUENCE: 10
tcgacttgta tgacatgata tc                                       22

<210> SEQ ID NO 11
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide sequence adding a silent BsrGI
      site.

<400> SEQUENCE: 11
gaaaaataac aaatgtacaa ccaagaatag t                             31

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence: Adds amino
      acids CIIS of RAS2 gene to carboxyl terminus of
      SLNI gene.

<400> SEQUENCE: 12
gtacatgtat tataagttaa taagaattca                               30
```

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Adds amino
acids CIIS of RAS2 gene to carboxyl terminus of
SLNI gene.

<400> SEQUENCE: 13
cgcgtgaatt cttattaact tataatacat                                    30

<210> SEQ ID NO 14
<211> LENGTH: 34
<212> TYPE: DNA
<213> ORGANISM: Artificial Sequence
<220> FEATURE:
<223> OTHER INFORMATION: Description of Artificial Sequence:
Oligonucleotides to isolate by PCR relevant
sequence from C/EBP clone.

<400> SEQUENCE: 14
ggccgctcga gcaaagccaa acagcgcaac gtgg                               34

<210> SEQ ID NO 15
<211> LENGTH: 35
<212> TYPE: DNA
<213> ORGANISM: Artificial Sequence
<220> FEATURE:
<223> OTHER INFORMATION: Description of Artificial Sequence:
Oligonucleotides to isolate by PCR relevant
sequence from C/EBP clone.

<400> SEQUENCE: 15
ggctagctag cttcaaggag ctctcaggca gctgg                              35

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence:
Oligonucleotide and complement to altercentral
leucine to proline.

<400> SEQUENCE: 16
gcgggtggaa cagccgagcc gtgaactgg                                     29

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:
Oligonucleotide used to subclone ECD of EGFR.

<400> SEQUENCE: 17
tatctcgagt gggacggccg gggcagcgct                                    30

<210> SEQ ID NO 18
<211> LENGTH: 29
<212> TYPE: DNA
<213> ORGANISM: Artificial Sequence
<220> FEATURE:
<223> OTHER INFORMATION: Description of Artificial Sequence:
Oligonucleotide used to subclone ECD of EGFR.

<400> SEQUENCE: 18

-continued

```
tagtgctagc ttaggcccat tcgttggac                                    29

<210> SEQ ID NO 19
<211> LENGTH: 68
<212> TYPE: DNA
<213> ORGANISM: Artificial Sequence
<220> FEATURE:
<223> OTHER INFORMATION: Description of Artificial Sequence:
      Oligonucleotide used to clone HOG1 open reading
      frame.

<400> SEQUENCE: 19
ccggccggcg cgccctcgag cggccgcgct ttgcagctac atgatcgctg acctttgttt    60
ccaccagc                                                             68

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence:
      Oligonucleotide used to clone HOG1 open reading
      frame.

<400> SEQUENCE: 20
ggccggcata tgaccactaa cgaggaattc attaggacac agatattcgg              50
```